United States Patent
Hampden-Smith et al.

(10) Patent No.: US 8,785,866 B2
(45) Date of Patent: Jul. 22, 2014

(54) COMPOSITIONS HAVING MULTIPLE RESPONSES TO EXCITATION RADIATION AND METHODS FOR MAKING SAME

(75) Inventors: Mark J. Hampden-Smith, Albuquerque, NM (US); Liam Noailles, Albuquerque, NM (US); Richard A. Einhorn, Albuquerque, NM (US)

(73) Assignee: Cabot Corporation, Boston, MA (US)

(*) Notice: Subject to any disclaimer, the term of this patent is extended or adjusted under 35 U.S.C. 154(b) by 147 days.

(21) Appl. No.: 13/548,364

(22) Filed: Jul. 13, 2012

(65) Prior Publication Data

US 2012/0273696 A1 Nov. 1, 2012

Related U.S. Application Data

(63) Continuation of application No. 11/773,696, filed on Jul. 5, 2007, now Pat. No. 8,257,612.

(51) Int. Cl.
*G01J 1/58* (2006.01)
*C09K 11/77* (2006.01)
*G02F 2/02* (2006.01)

(52) U.S. Cl.
CPC .................. *C09K 11/7769* (2013.01); *G02F 2/02* (2013.01)
USPC ............... 250/370.01; 250/336.1; 250/459.1

(58) Field of Classification Search
USPC ................................... 250/370.01
See application file for complete search history.

(56) References Cited

U.S. PATENT DOCUMENTS

| | | | |
|---|---|---|---|
| 3,322,682 A | 5/1967 | Thomson | |
| 3,373,302 A | 3/1968 | Barber | |
| 3,527,711 A | 9/1970 | Barber et al. | |
| 3,533,956 A | 10/1970 | Snitzer | |
| 3,574,130 A | 4/1971 | Mathers et al. | |
| 3,639,932 A | 2/1972 | Ferri et al. | |
| 3,725,811 A | 4/1973 | Murphy | |
| 5,003,181 A | 3/1991 | Morlotti | |
| 5,436,885 A * | 7/1995 | Okumura et al. | 369/275.2 |
| 5,611,958 A | 3/1997 | Takeuchi et al. | |
| 5,713,911 A | 2/1998 | Racenet et al. | |
| 6,180,029 B1 | 1/2001 | Hampden-Smith et al. | |
| 6,210,604 B1 | 4/2001 | Hampden-Smith et al. | |
| 6,402,987 B1 | 6/2002 | Srivastava et al. | |

(Continued)

FOREIGN PATENT DOCUMENTS

| | | |
|---|---|---|
| EP | 0622439 A | 11/1994 |
| EP | 1 184 440 A2 | 3/2002 |

(Continued)

OTHER PUBLICATIONS

Chen et al., "Photostimulated Luminescence and Dynamics of AgI and Ag nanoclusters in Zeolite", Phys. Rev B, vol. 65, 245404, pp. 1-8, May 2002.
Yen et al., Inorganic Phosphors: Compositions, Preparation and Optical Properties, pp. 465-470, 2004.
International Preliminary Report on Patentability for International Application No. PCT/US2008/069339, mailed on Jan. 5, 2010.

(Continued)

*Primary Examiner* — David Porta
*Assistant Examiner* — Djura Malevic

(57) ABSTRACT

The present invention relates to a composition having a first response to a first electromagnetic radiation and, after intermediate exposure to a second electromagnetic radiation, a second response to the first electromagnetic radiation, different from the first response. In one aspect, the composition exhibits a regenerated first response to the first electromagnetic radiation after exposure to a third electromagnetic radiation.

10 Claims, 3 Drawing Sheets

(56) References Cited

U.S. PATENT DOCUMENTS

| | | | |
|---|---|---|---|
| 6,888,303 B2 | 5/2005 | Cameron et al. | |
| 7,067,072 B2 | 6/2006 | Chen | |
| 7,175,206 B2 * | 2/2007 | Trantoul | 283/91 |
| 7,241,399 B2 * | 7/2007 | Haubold et al. | 252/301.4 R |
| 7,497,974 B2 | 3/2009 | Fan et al. | |
| 7,538,329 B2 * | 5/2009 | Chen et al. | 250/370.11 |
| 8,258,481 B2 * | 9/2012 | New et al. | 250/370.01 |
| 8,330,122 B2 * | 12/2012 | Smith et al. | 250/458.1 |
| 2001/0030313 A1 | 10/2001 | Oshima et al. | |
| 2002/0197510 A1 * | 12/2002 | Drew et al. | 428/690 |
| 2003/0047714 A1 | 3/2003 | Shimizu | |
| 2003/0064532 A1 * | 4/2003 | Chen | 438/3 |
| 2004/0000787 A1 * | 1/2004 | Vig et al. | 283/113 |
| 2004/0115385 A1 * | 6/2004 | Drew et al. | 428/64.1 |
| 2004/0118931 A1 * | 6/2004 | Selinfreund et al. | 235/492 |
| 2004/0178389 A1 | 9/2004 | Furusawa et al. | |
| 2004/0220298 A1 * | 11/2004 | Kozee et al. | 523/160 |
| 2005/0107607 A1 * | 5/2005 | Vig et al. | 544/37 |
| 2005/0112360 A1 | 5/2005 | Berger et al. | |
| 2005/0168124 A1 | 8/2005 | Justel et al. | |
| 2006/0022680 A1 | 2/2006 | Suginouchi et al. | |
| 2006/0078707 A1 * | 4/2006 | Selinfreund | 428/64.4 |
| 2006/0162497 A1 | 7/2006 | Kodas et al. | |
| 2006/0165898 A1 | 7/2006 | Kodas et al. | |
| 2006/0165910 A1 | 7/2006 | Kodas et al. | |
| 2006/0166057 A1 | 7/2006 | Kodas et al. | |
| 2006/0266276 A1 | 11/2006 | Shimura et al. | |
| 2006/0288926 A1 | 12/2006 | Kurata et al. | |
| 2007/0096057 A1 | 5/2007 | Hampden-Smith et al. | |
| 2008/0066090 A1 * | 3/2008 | Drew et al. | 720/718 |
| 2009/0008452 A1 * | 1/2009 | Selinfreund et al. | 235/454 |
| 2010/0176343 A1 * | 7/2010 | Chen et al. | 252/301.36 |

FOREIGN PATENT DOCUMENTS

| | | |
|---|---|---|
| EP | 1 593 651 A2 | 11/2005 |
| EP | 1 707 611 A2 | 10/2006 |
| EP | 1 887 068 A2 | 2/2008 |
| GB | 1 208 565 A | 10/1970 |
| JP | 2003 155480 A | 5/2003 |
| JP | 2004 091622 A | 3/2004 |
| WO | WO2005/062391 | 7/2005 |
| WO | WO2006/109238 | 10/2006 |

OTHER PUBLICATIONS

Hess J. W. Jr., et al., "Candoluminescence in Transition-Ion-Activated Oxide Phosphors", Journal of the Electrochemical Society USA, The Institution of Electrical Engineers, Stevenage, GB, Jan. 1974. vol. 121, No. 1, pp. 142-145.

Kaminskii A. A., et. al., Growth and Luminescence of LuAlO3—Ti 3+ Crystals, Soviet Physics—Doklady USA, The Institution of Electrical Engineers, Stevenage, GB, Aug. 1992, vol. 36, No. 8, pp. 422-423.

Strohhofer C. et al., "Enhancernent of Er 3+4I13/2 Population in Y2O3 by Energy Transfer to Ce3+", Optical Materials, Elsevier Science Publishers B.V., Amsterdam, NL, Sep. 1, 2001, vol. 17, No. 4, pp. 445-451, , XP004296823, ISSN: 0925-3467, DOI: DOI:10. 1016/S0925-3467(01)00103-3.

Van Die A., et al., "A Search for Luminescence of the Trivalent Manganese Ion in Solid Aluminates". Materials Research Bullentin, Elsevier, Kidlington, GB, Jun. 1, 1987, vol. 22, No. 6, pp. 781-788, XP024076662, ISSN: 0025-5408, DOI: DOI:10.1016/0025-5408(87)90032-8 [retrieved on Jun. 1, 1987].

Van Schaik W., et al., "Luminescence of Fe 3+ in LaPO4", Journal of Alloys and Compounds, Elsevier Sequoia, Lausanne, CH, Aug. 13, 1993, vol. 198, No. 1-2, pp. 69-72, XP)24176444, ISSN: 0925-8388, DOI: DOI: 10.1016/0925-8388(93)90147-F [retrieved on Aug. 13, 1993].

Pingbo, X., et al, "Photoluminescence Properties of Surface-Modified Nanocrystalline ZnS:Mn" Journal of Colloid and Interface Science, vol. 229, 2000, pp. 534-539, XP002498928.

Kravets, V., "Using Electron Trapping Materials for Optical Memory", Optical Materials, Elseview Science Publishers B.V. Amsterdam, NL, vol. 16, No. 3, Apr. 1, 2001, pp. 369-375, XP004231487.

Yen, William M., et al. (editors), "Inorganic Phosphors; Compositions, Preparation and Optical Properties", The CRC Press, Laser and Optical Science and Technology Series, ISBN 0-8493-1949-8 (alk. paper), Materials Index, pp. 469-465.

PCT Notification of Transmittal of the International Search Report and the Written Opinion of the International Searching Authority regarding International Application No. PCT/US2008/069339; mailed on Nov. 19, 2008.

* cited by examiner

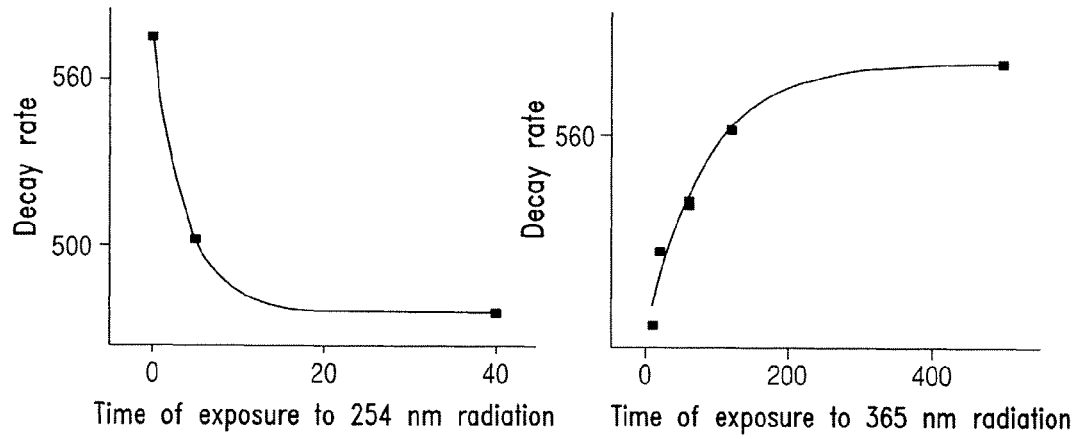
FIG. 4(a)
FIG. 4(b)
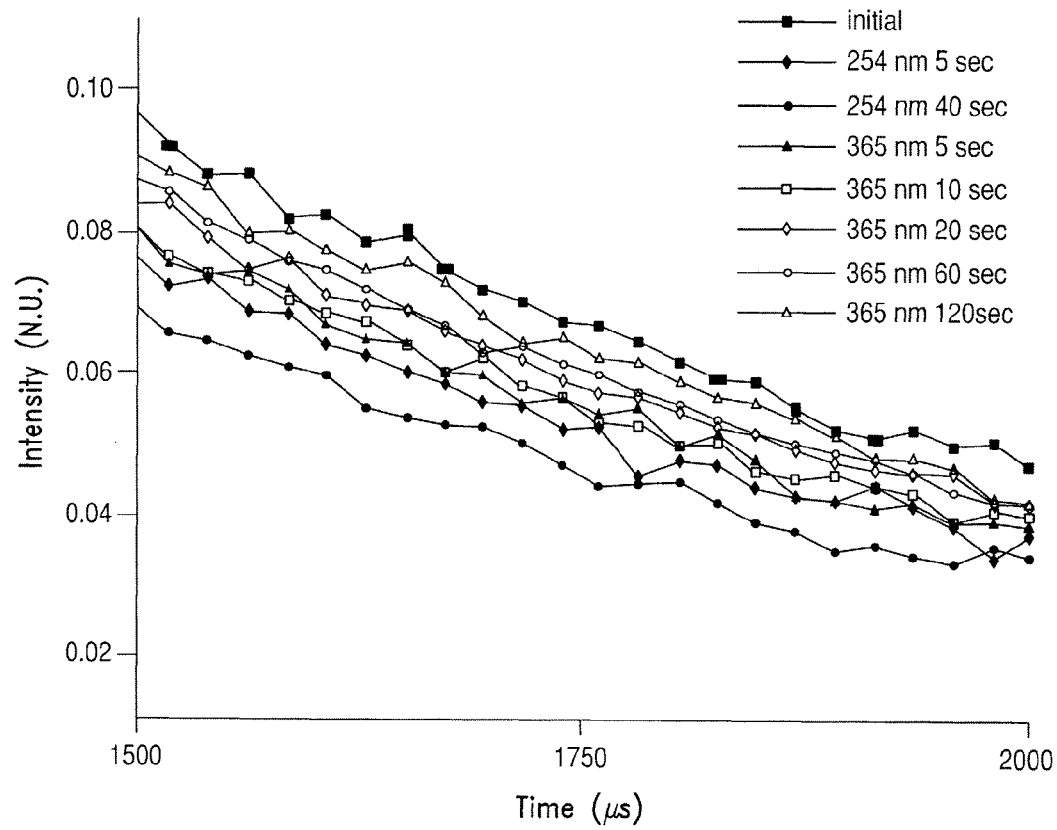
FIG. 4(c)

COMPOSITIONS HAVING MULTIPLE RESPONSES TO EXCITATION RADIATION AND METHODS FOR MAKING SAME

CROSS REFERENCE TO RELATED APPLICATION

This application is a continuation of and claims priority to U.S. application Ser. No. 11/773,696, filed on Jul. 5, 2007, hereby incorporated by reference in its entirety.

BACKGROUND OF THE INVENTION

1. Field of the Invention

The present invention relates generally to compositions having multiple responses to excitation radiation. In particular, the invention relates to compositions having a first response to a first electromagnetic radiation and, after intermediate exposure to a second electromagnetic radiation, a second response to the first electromagnetic radiation, different from the first response.

2. Discussion of Background Information

Conventional luminescent materials have one response (e.g., emission) to a given excitation by electromagnetic radiation. Luminescent materials may, for example, convert one wavelength to a second wavelength whether ultraviolet to visible, ultraviolet to infrared, visible to visible, visible to infrared, infrared to infrared, or infrared to visible. Luminescent materials may also emit near the wavelength they absorb.

The need exists for luminescent materials that can controllably emit different responses, e.g., emissions, to a single energy source. Such materials may be employed, for example, in security and laser applications. Luminescent materials with more than one response can also be employed as switches, e.g., in which a first response to excitation radiation may be controllably switched to a second response to the same excitation radiation by non-destructive and non-invasive means. This may be useful, for example, in optical computing, communication (switches and amplifiers), imaging, sensing and detection. However, conventional luminescent materials, as described above, emit only a single response to a single energy source or are not permeable (e.g., changeable). The need therefore exists for luminescent materials that provide more than one response to a single energy source.

SUMMARY OF THE INVENTION

The present invention provides a composition having a first response to a first electromagnetic radiation and, after intermediate exposure to a second electromagnetic radiation, a second response to the first electromagnetic radiation, different from the first response. In one embodiment, the composition comprises: (a) a host material, e.g., host lattice; (b) an emissive material; and (c) an emission modifier. The composition is particularly well-suited for being incorporated into a security feature for authenticating an article.

In another aspect, the invention relates to a regenerable composition, wherein the composition has a first form having a first response to a first electromagnetic radiation and a second form having a second response to the first electromagnetic radiation, the composition being repeatably transformable from the first form to the second form upon application of a second electromagnetic radiation.

In still another aspect, the invention relates to a regenerable composition comprising a plurality of forms having a plurality of responses, wherein: (a) the composition is transformable from a first form having a first response to a second form having a second response upon application of electromagnetic radiation of wavelength $\lambda_A$; and (b) the composition is transformable from the second form having the second response to a third form having a third response upon application of electromagnetic radiation of wavelength $\lambda_B$; and (c) the composition is transformable from the third form having the third response to the first form having the first response upon application of electromagnetic radiation of wavelength $\lambda_{regen}$.

BRIEF DESCRIPTION OF THE DRAWINGS

The present invention will be better understood in view of the appended non-limiting figures, in which:

FIG. 4(a) is a graph demonstrating decay rate for a composition manufactured according to Example 3 after exposure to 254 nm radiation; FIG. 4(b) is a graph demonstrating the regenerability of the composition from Example 3; and FIG. 4(c) is an expansion of the decay curves for the composition of Example 3 after exposure to first and second electromagnetic radiation for various times.

DETAILED DESCRIPTION OF THE INVENTION

Composition

In one embodiment, the invention is directed to a composition, e.g., a luminescent composition, that exhibits a first response to a first electromagnetic radiation and, after intermediate exposure to a second electromagnetic radiation, a second response to the first electromagnetic radiation, different from the first response. In one embodiment, the composition exhibits a regenerated first response to the first electromagnetic radiation after exposure to a third electromagnetic radiation (a "regenerating" electromagnetic radiation). The composition optionally comprises substantially spherical particles having a volume average particle size of less than about 15 µm, and a particle size distribution such that at least about 90 volume percent of the particles are not larger than twice the average particle size.

In another embodiment, the composition has a first form having a first response to a first electromagnetic radiation and a second form having a second response to the first electromagnetic radiation, the composition being transformable, e.g., repeatably transformable, from the first form to the second form upon application of a second electromagnetic radiation.

Figure 1:
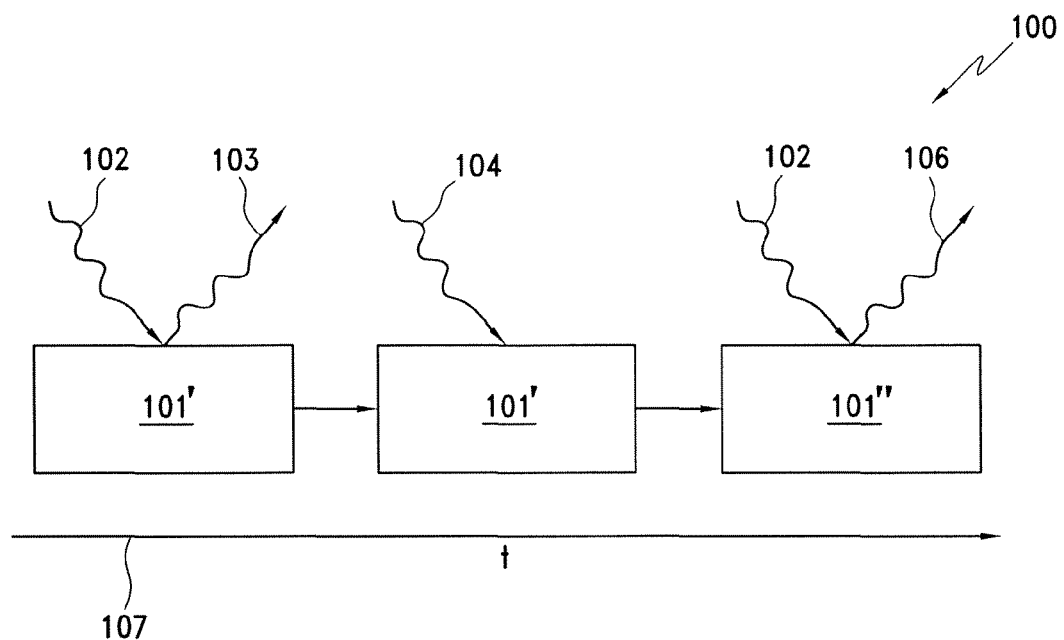
FIG. 1 presents the progression of a composition according to one embodiment of the present invention in which the composition yields different responses to first electromagnetic radiation after intermediate exposure to a second electromagnetic radiation.

This embodiment is illustrated in FIG. 1, which shows the progression, generally designated progression 100, of the composition 101 of the present invention over time (t) 107, as the composition 101 is subjected to a first electromagnetic radiation 102 and a second electromagnetic radiation 104. As shown, the composition 101 begins the progression 100 having first form 101'. When excited by the first electromagnetic radiation 102 having a first intensity and a first wavelength, the composition having first form 101' emits a first response 103. If the composition having first form 101' is subjected to a second electromagnetic radiation 104 having a second intensity and a second wavelength, the composition is transformed from the first form 101' to a second form 101". When excited by the first electromagnetic radiation 102 having the first intensity and the first wavelength, the composition having second form 101" emits a second response 106, which is different from the first response 103. According to the present invention, when the inventive composition is employed in a security feature, the specific differences between the first response 103 and the second response 106 (e.g., difference in intensity and/or wavelength(s)) preferably are known such that it becomes possible to authenticate the security feature as well as any commercial products, banknotes, or other items associated therewith.

In another embodiment, the composition is transformable, e.g., repeatedly transformable, from the second form back to the first form upon application of a third electromagnetic radiation (a regeneration electromagnetic radiation, e.g., of wavelength $\lambda_{regen}$). In some embodiments, the second form of the composition may be, for example, a photooxidized or a photoreduced form of the first form of the composition, as discussed in greater detail below.

Figure 2:
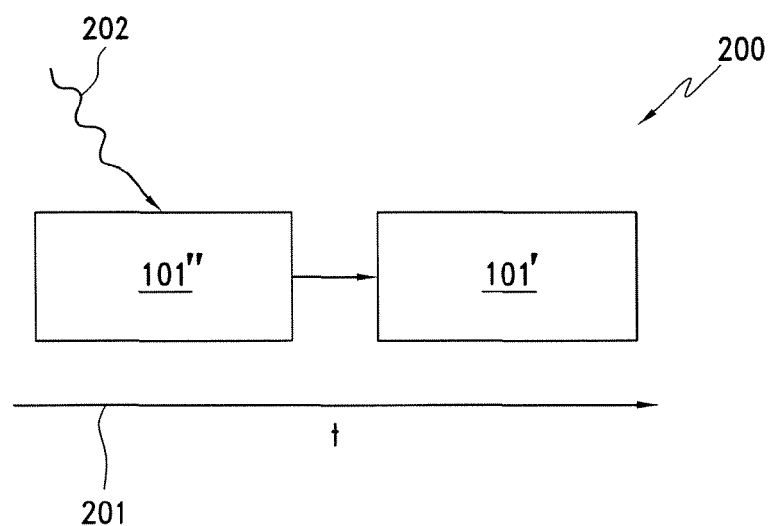
FIG. 2 illustrates the regenerability of compositions according to some embodiments of the present invention.

The optional regenerable aspect of the compositions of the present invention is illustrated in FIG. 2 over time (t) 201. As shown in progression 200, when exposed to a regeneration electromagnetic radiation 202 (e.g., having a regeneration intensity and a regeneration wavelength ($\lambda_{regen}$)), the composition having second form 101" is transformed to the composition having the first form 101'. The regenerated composition having first form 101' may then undergo (optionally, repeatedly undergo) the process described with reference to FIG. 1. The ability to couple the inventive aspects illustrated in FIGS. 1 and 2 is highly desirable in security applications as it provides the ability to repeatably determine whether a security feature and its corresponding article are authentic.

In one embodiment, either or both the first response and/or the second response comprise a non-visible form of electromagnetic radiation. For example, either or both the first response and/or the second response may comprise electromagnetic radiation in the UV or IR spectrums. In another embodiment, either or both the first response and/or the second response comprise electromagnetic radiation in the visible spectrum. Of course, combinations of various electromagnetic radiation types may also be employed.

In one embodiment, the first response and the second response comprise a non-colorimetric response. Conversely, the first response and the second response may comprise a colorimetric response. As used herein, the term "colorimetric response" means that the composition exhibits a change in color after exposure to the second electromagnetic radiation (transformation radiation). In this aspect, the first response is a first color and the second response is a second color, different from the first color. This change in color may be appreciable to the naked eye, and/or may be detectable by an instrument. As before, the composition optionally exhibits a regenerated first response to the first electromagnetic radiation after exposure to a third electromagnetic radiation (regeneration radiation).

The first electromagnetic radiation that is used to generate the first response and the second response preferably comprises low-intensity electromagnetic radiation in the infrared spectrum. As used herein, the term "low-intensity electromagnetic radiation" means electromagnetic radiation with an intensity no greater than 2500 mW/cm$^2$, e.g., no greater than 2000 mW/cm$^2$, no greater than 1500 mW/cm$^2$, or no greater than 1000 mW/cm$^2$. It is contemplated, however, that the first electromagnetic radiation may comprise high-intensity electromagnetic radiation. As used herein, the term "high-intensity electromagnetic radiation" means electromagnetic radiation with an intensity of greater than 2500 mW/cm$^2$, e.g., greater than 3000 mW/cm$^2$, or greater than 3500 mW/cm$^2$. Optionally, the electromagnetic radiation has an intensity of from 2500 mW/cm$^2$ to 5000 mW/cm$^2$, e.g., from about 2500 mW/cm$^2$ to 4000 mW/cm$^2$, from 2500 mW/cm$^2$ to 3000 mW/cm$^2$, or from 3000 mW/cm$^2$ to 4000 mW/cm$^2$. Preferably, the first electromagnetic radiation has a wavelength of from about 700 nm to about 1500 nm, e.g., from about 700 nm to about 1100 nm, or from about 800 nm to about 1000 nm. The first electromagnetic radiation may be obtained, for example, from a light emitting diode (LED) (e.g., a UV LED, IR LED, Blue LED, Visible emission LED, etc.).

The second electromagnetic radiation to which the composition is exposed, and which transforms the composition from the first form to the second form, preferably comprises high-intensity electromagnetic radiation, such as radiation in the ultraviolet spectrum. In one embodiment, the second electromagnetic radiation has a wavelength from about 150 nm to about 300 nm, e.g., from about 200 nm to about 300 nm, or from about 250 nm to about 270 nm. The second electromagnetic radiation may be obtained, for example, from a UV-lamp, a xenon lamp, from ambient light (e.g., fluorescent room light) or from sunlight.

As indicated above, in one aspect, the composition is transformable, e.g., repeatedly transformable, from the second form to the first form upon application of a third electromagnetic radiation (regenerating radiation). In one embodiment, the third electromagnetic radiation comprises high-intensity electromagnetic radiation in the infrared spectrum. Preferably, the third electromagnetic radiation has a wavelength in the range of from about 900 nm to about 10,000 nm, e.g., from about 1,000 nm to about 7,000 nm or from about 1,300 nm to about 6,000 nm. In another embodiment, the third electromagnetic radiation comprises high-intensity electromagnetic radiation in the ultraviolet spectrum. In this aspect, the third electromagnetic radiation preferably has a wavelength from about 300 nm to about 400 nm, e.g., from about 320 nm to about 380 nm, or from about 350 nm to about 370 nm. The third electromagnetic radiation may be obtained, for example, from a Sylvania 120V/125W lamp if high-intensity infrared radiation is desired or from a UV lamp (e.g., a model UVGL-25 Minerlight® multiband UV-254/364 lamp) if high-intensity ultraviolet electromagnetic radiation with a wavelength from about 300 nm to about 400 nm is desired. Of course, other electromagnetic radiation sources may also be employed to provide the third electromagnetic radiation.

As discussed above, the composition preferably has a plurality of responses and/or forms. The invention is not limited to compositions having two responses and/or forms. For example, in some aspects, the invention is directed to a composition comprising more than 2, e.g., 3, 4, 5, 6, or more forms and has a plurality of responses (e.g., each form having a different response).

In one example, the composition has three (or more) forms. In this aspect, the composition is transformed from a first form having a first response to a second form having a second response upon application of electromagnetic radiation of wavelength $\lambda_A$. The composition is then transformed from the second form having the second response to a third form having a third response upon application of electromagnetic radiation of wavelength $\lambda_B$. In this aspect, the first response, the second response and the third response preferably are responses to the same type of excitation radiation, which is ideally different from the transformation electromagnetic radiation of wavelengths $\lambda_A$ and $\lambda_B$. Optionally, the composition is transformable from the third form (and/or from the second form) back to the first form upon application of a regeneration electromagnetic radiation of wavelength $\lambda_{regen}$ for time $t_{regen}$. $t_{regen}$ may vary depending, for example, on the intensity of the regeneration electromagnetic radiation employed; generally, the greater the intensity of the regeneration radiation, the lower $t_{regen}$, and vice versa. It is contemplated that multiple applications of the regeneration electromagnetic radiation of wavelength $\lambda_{regen}$ for times less than $t_{regen}$ may be employed to gradually regenerate the composition back to its first form, preferably in a known way. In this latter aspect, the regenerating of the composition may occur in a continuous manner or in a quantized (step-wise) manner. This aspect is discussed below with reference to Example 7 and FIG. 3.

Of course, additional forms may also be employed. For example, the composition having the third form may be transformed upon application of electromagnetic radiation of wavelength $\lambda_C$ to a composition having a fourth form having a fourth response (to the excitation radiation). In an optional embodiment, the composition is transformable from the fourth form having the fourth response (and/or from the third form and/or from the second form) to the first form having the first response upon application of electromagnetic radiation of wavelength $\lambda_{regen}$ for regeneration time $t_{regen}$.

Ideally, $\lambda_A$, $\lambda_B$, optional $\lambda_C$, and optional $\lambda_{regen}$ are each different from one another. Optionally, $\lambda_A$ is electromagnetic radiation having a wavelength of less than about 300 nm, e.g., from about 150 nm to about 300 nm, from about 200 nm to about 300 nm, or from about 250 nm to about 270 nm. In a preferred embodiment, $\lambda_A$ comprises low-intensity electromagnetic radiation. In still another embodiment, one or more of $\lambda_B$, $\lambda_C$, and $\lambda_{regen}$ comprises electromagnetic radiation having a wavelength of greater than about 300 nm; for example, one or more of $\lambda_B$, $\lambda_C$, and $\lambda_{regen}$ may comprise electromagnetic radiation having a wavelength of from about 300 nm to about 400 nm. In a preferred embodiment, $\lambda_B$, $\lambda_C$, and $\lambda_{regen}$ each comprises high-intensity electromagnetic radiation. In still another embodiment, $\lambda_{regen}$ comprises electromagnetic radiation having a wavelength of from about 900 nm to about 10,000 nm, e.g., from about 1,000 nm to about 7,000 nm, or from about 1,300 nm to about 6,000 nm. In another embodiment, $\lambda_{regen}$ comprises electromagnetic radiation having a wavelength of from about 300 nm to about 400 nm, e.g., from about 320 nm to about 380 nm, or from about 350 nm to about 370 nm. In a preferred embodiment, $\lambda_{regen}$ comprises high-intensity electromagnetic radiation Structurally, in a preferred aspect, the inventive composition comprises a host material, e.g., host lattice, an emissive material, and an emission modifier. The composition optionally further comprises a sensitizer. As used herein, the teem "host material" means a material that houses or contains the emissive material. Preferably, the host material comprises a host lattice. An "emissive material" is a material that is capable of emitting electromagnetic radiation. Emission of electromagnetic radiation by the emissive material results after the electronic excited state of the emissive material is populated. Optionally, the composition comprises a plurality of different emissive materials, e.g., 2, 3, 4, 5 or more emissive materials. An "emission modifier" is a material that changes or is capable of changing the emission of the emissive material. A "sensitizer" is a material that is capable of absorbing incident radiation and transferring the energy to the emissive material. The presence of a sensitizer typically will result in a more efficient emission from the emissive material. Thus, the excited state of the emissive material may be populated by the absorption of electromagnetic radiation directly by the emissive material and/or by absorption by a sensitizer and subsequent transferring of energy to the emissive material. In some aspects, a single material may have multiple functions. For example, in some circumstances, a lattice may act as a host material as well as a sensitizer (e.g., incident radiation may be initially absorbed into a charge transfer band of the lattice). Similarly, an emission modifier may also act as a sensitizer. As a further example, a sensitizer will also typically act as an emissive material to at least some extent unless the energy transfer from the sensitizer is particularly efficient.

In various aspects, the emissive material may comprise an ion, such as a rare earth metal ion or a transition metal ion. In some aspects, the emissive material may comprise the host material itself (e.g., as a defect in the host material) or a molecule. In a preferred embodiment, the emissive material comprises a lanthanide, e.g., a lanthanide ion. In some embodiments, the oxidation state of the lanthanide element emissive material is such that the ion has no accessible, open-shell d electrons; that is, all d electrons are in closed shells.

In one embodiment, the emissive material comprises a lanthanide selected from the group consisting of yttrium, cerium, praseodymium, neodymium, samarium, europium, terbium, dysprosium, holmium, erbium, thulium and ytterbium; or the lanthanide is selected from the group consisting of cerium, praseodymium, neodymium, samarium, europium, dysprosium, erbium, thulium and ytterbium, with ytterbium being particularly preferred. In some embodiments, the emissive material comprises a semiconductor such as silicon, e.g., doped silicon, a Group III/V compound (e.g., Indium Phosphide) or a Group II/VI compound (e.g., Cadmium Selenide). In another embodiment, the emissive material comprises a transition metal. In some non-limiting examples, the emissive material comprises a metal selected from the group consisting of manganese, chromium, titanium, and niobium. In a preferred aspect, the emissive material comprises chromium, manganese, vanadium or iron. Non-limiting examples of host material/emissive material combinations comprising a transition metal include $Y_3Al_5O_{12}:Cr^{3+}$, $ZnB_2O_4:Mn^{2+}$, $Mg_3SiO_3F_4:Ti^{4+}$, and $LuTaO_4:Nb^{5+}$.

Other emissive material/host material combinations that may be used in the present invention include emissive materials such as those that are disclosed in *Inorganic Phosphors: Compositions, Preparation and Optical Properties* 465-470 (William M. Yen & Marvin J. Weber eds., 2004), the entire contents of which are incorporated herein by reference. Some preferred combinations include, for example, $BaAl_2O_4$:Eu, $CaAl_2O_4$:Ce, $(ErCl_3)_{0.25}(BaCl_2)_{0.75}$, GaN:Zn, $KAl_{11}O_{17}$:Tl, $LaAl_3B_4O_{12}$:Eu, $MgAl_2O_4$:Mn, $Na_3Ce(PO_4)_2$:Tb, $SrAl_{12}O_{19}$:Ce, Mn, $ThO_2$:Eu, $YAl_3B_4O_{12}$:Bi, and $ZnAl_2O_4$:Mn. Silicates of the aforementioned emissive materials, as well as emissive materials comprising lead (Pb) and emissive materials of the formula $Ln_xO_y$ are also contemplated, where Ln is a Lanthanide.

The amount of emissive material present in the composition can range from about 0.1 to about 99 mole %, e.g., from about 1 to about 30 mole %, or from about 5 to about 25 mole %, based on the total moles of the site substituted by the emissive material within the host material.

Typically, the emission modifier is turned "on" or "off" by intermediate exposure to transformation radiation. For example, as described above, the emission modifier may be turned "on" by the above-described second electromagnetic radiation or may be turned "off" by the above-described regenerating electromagnetic radiation of wavelength $\lambda_{regen}$ and regenerating time $t_{regen}$. Thus, while in its "on" state, the emission modifier interacts with the emissive material, but the emission modifier does not interact (or interacts in a different way) with the emissive material while in its "of" state. A non-limiting example of this is where an excited state ion, acting as an emission modifier, enables a non-radiative pathway for the excited state of an emissive material to decay. In this case, the response (e.g., luminescent decay) may be different depending on whether the emission modifier is in its "on" excited state, or "off" ground state.

How the emission modifier varies the response of the emissive material also may vary. For example, in various embodiments, the emission modifier may vary one or more of: the absorption wavelength, absorption bands, color, luminescent emission intensity, luminescent emission wavelength, luminescent emission decay, luminescent emission persistence, luminescent excitation uptake and luminescent excitation wavelength of the emissive material. In some preferred aspects, the emission modifier that is present in the composition affects the intensity and/or the persistence of the emission of the emissive material and/or the wavelength of the electromagnetic radiation emitted by the emissive material. In various embodiments, the emission modifier includes a localized charge center, electron hole, oxygen vacancy, excited state species, photoooxidized species, photoreduced species, or phonon mode.

In one embodiment, the emission modifier comprises a lanthanide, e.g., a lanthanide ion. In one embodiment, the emission modifier comprises a lanthanide selected from the group consisting of cerium, holmium, praseodymium, neodymium, samarium, europium, dysprosium, erbium, thulium, and ytterbium, with cerium being particularly preferred. In some embodiments, the emission modifier can be present as an oxygen-containing compound, such as a metal oxide, a silicate, borate, oxysulfide or aluminate. In another embodiment, the emission modifier comprises a transition metal. In a non-limiting example, the emission modifier comprises chromium, molybdenum, titanium, manganese, iron, nickel or niobium.

While in a preferred embodiment the emission modifier is a chemical compound that comprises ions, the emission modifier can also be a defect in the host material, e.g., host lattice, that is created when the composition is exposed to the second electromagnetic radiation. Thus, a defect in the host material may act as the emission modifier. In this manner, the host material (or region(s) thereof) may act as the emission modifier. Non-limiting examples of the host material acting as an emission modifier is where the host material changes its structure thereby changing the emissive material's response to the first electromagnetic radiation, or where new phonon modes are occupied that change the emissive material's response to the first electromagnetic radiation when the host material, e.g., host lattice, absorbs the second electromagnetic radiation.

In another aspect, a fraction of the emissive material in the composition acts as the emission modifier. For example, a fraction of the emissive material may enter an excited state that has a different response to the first electromagnetic radiation after absorbing the second electromagnetic radiation. In one embodiment, a fraction of the emissive material may be switched to become the emission modifier and act upon the remaining emissive material to change the emissive material's response to the first electromagnetic radiation.

As indicated above, the emission modifier preferably is turned on by the second electromagnetic radiation. The defect, excited state, entity, etc., may be created upon exposure to the second electromagnetic radiation. In one embodiment, the defect or entity is removed upon exposure to the regeneration electromagnetic radiation. The emissive material may have any number of permutations due to the number or type of defect or entity. In one embodiment, the second electromagnetic radiation, the third electromagnetic radiation, or another electromagnetic radiation such as a fourth electromagnetic radiation transmutates the emissive material to any number of forms by changing the number or type of emissive modifiers, defects or entities.

The amount of emission modifier present in the composition can range from about 0.0001 mole % to about 10 mole %, e.g., from about 0.001 mole % to about 10 mole %, from about 0.01 mole % to about 5 mole %, from about 0.1 mole % to about 3 mole %, or from about 0.001 mole % to about 1 mole %, of the total composition.

The identity of the host material, e.g., host lattice, may be critical to the performance of the composition because it influences the electronic environment of the emissive material and the non-radiative pathways for the decay for electronic excited states. In particular, any host material may be used herein if it is possible to incorporate at least one type of emissive material into the host material. Examples of host materials that may be useful include oxides, oxysulfides, sulfides, fluorides, phosphates, silicates, borosilicates, aluminates, thioaluminates, gallates, thiogallates, germanates, stannates, vanadates, molybdates, tungstates and borates of at least one metal. In a preferred embodiment, the host material comprises a sulfide, a fluoride, an oxynitride, an oxysulfide or an oxyfluoride. The host material preferably comprises a metal selected from Groups 2, 3, 12, 13, 14 and 15 of the Periodic Table and the lanthanide elements, and preferably is selected from lanthanum, lutetium, yttrium, gadolinium, zinc, magnesium, calcium, strontium, and barium. In one embodiment, the lattice comprises an oxygen-containing compound selected from the group consisting of $Y_2O_3$, $Y_2GdAl_5O_{12}$, $Y_3Al_5O_{12}$, $Y_3Al_4GaO_{12}$, $YBO_3$, $Y_{0.76}Gd_{0.24}BO_3$, $YPO_4$, $YSiO_5$, $LaBO_3$, $LaPO_4$, $La_2O_3$, $LaAlO_3$, $LuAlO_3$, $La_3Al_5O_{12}$, $LaSiO_5$, and $ReP_5O_{14}$, wherein Re is a Rare Earth metal. In another embodiment, the host material comprises a glass. Host materials comprising borosilicate glasses and $SrAl_2O_4$ are also contemplated.

In one embodiment, the composition further comprises a UV-blocking material. As used herein, the term "UV-blocking material" is any material that substantially blocks electromagnetic radiation in the UV spectrum from causing the emission modifier present in the composition to affect the intensity and/or the persistence of the emission of the emissive material. The UV-blocking material optionally is in the form of a coating on core particles comprising the composition. Non-limiting examples of UV-blocking materials include materials comprising titanium oxide, zinc oxide, para-aminobenzoic acid (PABA) and its esters, benzophenones, cinnamates, salicylates, dibenzoylmethanes, anthranilates, methylbenzylidene, octyltriazone, and octocrylene.

In another embodiment, the UV-blocking material may partially or substantially cover a feature, e.g., a security feature, comprising the composition. As used herein, the term "feature" includes any two- or three-dimensional structure including, but not limited to, a line, a shape, an image, a dot, a patch, and a continuous or discontinuous layer (e.g., coating). When the UV-blocking material partially covers the feature, the second response to the first electromagnetic radiation from the feature, even after intermediate exposure to a second electromagnetic radiation, is not observed (or is observed to a lesser extent) in those regions of the feature that are covered by the UV-blocking material. In this aspect, the second response is preferably only observed in those regions of the feature that are not covered by the UV-blocking material. When the UV-blocking material substantially covers the security feature, the first response to the first electromagnetic radiation by the security feature, even after intermediate exposure to a second electromagnetic radiation, is observed and the second response is not substantially observed. Optionally, the UV-blocking material is deposited in a direct write printing process, e.g., an ink jet printing process. In this aspect, the UV-blocking material may be printed in a pattern that forms an image displaying variable information.

As-synthesized, the composition preferably comprises a powder batch with particles having a small average size. Although the preferred average size of the particles will vary according to the application of the powder, the average particle size of the particles optionally is less than about 15 µm, e.g., less than about 10 µm, less than about 5 µm, less than about 3 µm, or from about 5 to 500 nanometers, e.g., from about 7 to about 15 nanometers, from about 40 to about 150 nanometers, from about 50 to about 300 nm, or from about 250 to about 500 nanometers. In one embodiment, the average particle size of the particles is from about 0.1 µm to about 3 µm, or about 2 µm. As used herein, the average particle size is the volume average particle size.

The powder batch of particles also optionally has a narrow particle size distribution, such that the majority of particles are substantially the same size. Preferably, at least about 90 volume percent of the particles and more preferably at least about 95 volume percent of the particles are not larger than twice the average particle size. Thus, for example, when the average particle size is about 2 µm, it is preferred that at least about 90 volume percent of the particles are not larger than 4 µm; or that at least about 95 volume percent of the particles are not larger than 4 µm. Further, it is preferred that at least about 90 volume percent of the particles, and more preferably at least about 95 volume percent of the particles, are not larger than about 1.5 times the average particle size. Thus, for example, when the average particle size is about 2 µm, it is preferred that at least about 90 volume percent of the particles are not larger than about 3 µm; or that at least about 95 volume percent of the particles are not larger than about 3 µm.

The particles can be substantially single crystal particles or may be comprised of a number of crystallites. Preferably, the particles are highly crystalline with the average crystallite size approaching the average particle size such that the particles are mostly single crystals or are composed of only a few large crystals. The average crystallite size of the particles is preferably at least about 25 nanometers, more preferably is at least about 40 nanometers, even more preferably is at least about 60 nanometers and most preferably is at least about 80 nanometers. In one embodiment, the average crystallite size is at least about 100 nanometers, for example, at least about 200 nanometers, or at least about 500 nanometers. As it relates to particle size, the average crystallite size is preferably at least about 20 percent, more preferably at least about 30 percent and most preferably is at least about 40 percent of the average particle size.

The particles can be substantially spherical in shape. That is, the particles optionally are not jagged or irregular in shape. Although the particles optionally are substantially spherical, the particles may become faceted as the crystallite size increases and approaches the average particle size. In other aspects, the particles are substantially non-spherical.

The particles optionally have a high degree of purity; that is, the particles optionally contain a low level of impurities (i.e., materials that are not intended in the final product). The level of impurities in the powders comprising the particles is preferably not greater than about 1 atomic percent, e.g., not greater than about 0.1 atomic percent, or not greater than about 0.01 atomic percent. In addition, the surfaces of the particles optionally are smooth and clean with a minimal deposition of contaminants on the particle surface. For example, the outer surfaces are not contaminated with surfactants, as is often the case with particles produced by liquid precipitation routes.

The density of the particles comprised in the composition may be controlled to vary between highly dense particles, to porous particles, to hollow particles. In addition, the particles optionally have a low surface area. If the particles are substantially spherical, the total surface area for a given mass of powder is reduced. Further, the optional elimination of larger particles from the powder batches eliminates the porosity that is associated with open pores on the surface of such larger particles. If the large particles are eliminated from the batch, the powder advantageously has a lower surface area. Surface area is sometimes measured using a Brunauer, Emmett, and Teller (BET) nitrogen adsorption method which is indicative of the surface area of the powder, including the surface area of accessible surface pores on the surface of the powder. For a given particle size distribution, a lower value of a surface area per unit mass of powder indicates solid or non-porous particles. Decreased surface area reduces the susceptibility of the powders to adverse surface reactions, such as degradation from moisture. This characteristic can advantageously extend the useful life of the powders.

Preferably, the powder is substantially unagglomerated. One advantage of unagglomerated particles is that they often result in free-flowing powders. In some embodiments, however, the particles comprise agglomerated nanoparticles. Hard agglomerates are physically coalesced lumps of two or more particles that behave as one large particle. Agglomerates are disadvantageous in most applications of powders. In one embodiment, no more than about 1 volume percent of the particles in the powder batch of the present invention are in the form of hard agglomerates; for example, not more than about 0.5 volume percent of the particles are in the form of hard agglomerates; or not more than about 0.1 volume percent of the particles are in the form of hard agglomerates.

According to one embodiment of the present invention (similar to the UV-blocking-material-coated particles described above), the particles comprise a core and a surface cap or coating disposed thereon. In this aspect, the cap or coating preferably substantially encapsulates the outer surface of the core. In one aspect, the core comprises the emissive material (and preferably the host material), and the cap or coating comprises the emission modifier. In another aspect, the core comprises the emission modifier and the cap or coating comprises the emissive material (and optionally the host material). In yet another embodiment, the core comprises both the emissive material and the emission modifier (and optionally the host material). The sensitizer, if present, may be disposed in the core, in the cap/coating or in both the core and the cap/coating.

The function of the cap/coating may vary widely. In one aspect, the cap/coating assists in reducing degradation of the emissive material and/or emission modifier (e.g., in the core) due to moisture or other influences and can also create a diffusion barrier that, for example, inhibits leaching of the emissive material or emission modifier (or optional sensitizer) from the host material, which would adversely alter the characteristics of the composition. In this aspect, the cap/coating optionally comprises a hydrophobic material. The cap or coating optionally controls the surface energy levels of the particles. In one embodiment, the cap/coating can be the cause of the first response and/or the second response; for example, in one aspect, the junction between the cap/coating and the underlying core acts as the emissive material due to a difference in the energy levels of the core material and the cap/coating material.

The cap/coating, for example, can be a metal, metal oxide or other inorganic compound such as a metal sulfide, or can be an organic compound. For example, a metal oxide cap or coating can be used, such as a metal oxide selected from the group consisting of $SiO_2$, $MgO$, $Al_2O_3$, $ZnO$, $SnO_2$ or $In_2O_3$. In one embodiment, the cap or coating comprises $SiO_2$ and/or $Al_2O_3$. Metal coatings, such as copper, and phosphate coatings, such as zirconium phosphate or aluminum phosphate, can also be advantageous for use in some applications. See, for example, U.S. Provisional Patent Application Ser. No. 60/805,185 filed Jun. 19, 2006, the entirety of which is incorporated herein by reference.

In one embodiment, the cap or coating encapsulates an entire particle core, but should be sufficiently thin that the coating does not interfere with light transmission. In one embodiment, the cap or coating has an average thickness of at least about 2 nanometers; for example, at least about 5 nanometers, but not greater than about 200 nanometers; or not greater than about 100 nanometers; or not greater than about 50 nanometers. In one embodiment, the cap or coating has a thickness of from about 2 to about 50 nanometers, such as from about 2 to about 10 nanometers. Further, the particles can include more than one cap or coating substantially encapsulating the particles to achieve the desired properties.

The cap or coating, either particulate or non-particulate, can also include a pigment or other material that alters the light characteristics of the emissive material and/or emission modifier. Red pigments can include compounds such as the iron oxides ($Fe_2O_3$), cadmium sulfide compounds (CdS) or mercury sulfide compounds (HgS). Green or blue pigments include cobalt oxide (CoO), cobalt aluminate ($CoAl_2O_4$) or zinc oxide (ZnO). Pigment coatings are capable of absorbing selected wavelengths of light emitted by the emissive material and/or emission modifier, thereby acting as a filter to improve the color contrast and purity.

In addition, the particles can be capped or coated with an organic compound, such as PMMA (polymethylmethacrylate), polystyrene or similar organic compounds, including surfactants that aid in the dispersion and/or suspension of the particles in a flowable medium. The organic coating is preferably not greater than about 100 nanometers thick and is substantially dense and continuous about the particle. The organic coatings can advantageously prevent corrosion of the particles and also can improve the dispersion characteristics of the particles in a paste or other flowable medium.

The coating can also be comprised of one or more monolayer coatings, such as from about 1 to 3 monolayer coatings. A monolayer coating is formed by the reaction of an organic or an inorganic molecule with the surface of the particles to form a coating layer that is essentially one molecular layer thick. In particular, the formation of a monolayer coating by reaction of the surface of the powder with a functionalized organosilane such as halo- or amino-silanes, for example hexamethyldisilazane or trimethylsilylchloride, can be used to modify and control the hydrophobicity and hydrophilicity of the powders. Metal oxides (e.g. ZnO or $SiO_2$) or metal sulfides (e.g. $Cu_2S$) can also be formed as monolayer coatings. Monolayer coatings can allow for greater control over the dispersion characteristics of the powder in a wide variety of paste compositions and other flowable mediums.

The monolayer coatings may also be applied to powders that have already been coated with an organic or inorganic coating, thus providing better control over the corrosion characteristics (through the use of a thicker coating) as well as dispersibility (through the use of a monolayer coating) of the powder.

Method of Making the Particles Comprised in the Composition

The particles comprising the composition of the invention can be produced by any known method that generates particles having the characteristics described above and the desired size, size distribution and morphology. Suitable methods include spray pyrolysis and pyrolysis using a flame reactor, as discussed below. In addition, a modification of these methods can be used in a gas dispersion process to produce nanoparticles dispersed in a matrix.

Spray pyrolysis involves initially preparing a liquid feed containing at least one precursor for the desired particulate product in a liquid medium, converting the liquid feed to aerosol form, in which droplets of the liquid feed are dispersed in and suspended by a carrier gas, and then removing the liquid from the droplets to permit formation of the desired particles in a dispersed state. The particles are then collected in a particle collector to recover the particulate product. In one embodiment, the feed precursor is pyrolyzed in a furnace to make the particles. While still in a dispersed state, the particles are subjected to compositional or structural modification, if desired. Compositional modification may include, for example, coating the particles. Structural modification may include, for example, crystallization, recrystallization or morphological alteration of the particles. Further details of the spray pyrolysis process can be found in U.S. Pat. No. 6,180,029, and in U.S. Published Application US 20070096057, filed Oct. 26, 2006, the entire contents of which are hereby incorporated herein as if set forth herein in full. See also U.S. Published Applications US 20060166057; US 20060165898; US 20060165910; and US 20060162497, which were filed on Jan. 20, 2006, the entireties of which are incorporated herein by reference.

In the flame reactor process, a nongaseous precursor of at least one component of the desired particulate composition is introduced into a flame reactor heated by at least one flame. The nongaseous precursor is introduced into the flame reactor in a very hot zone, also referred to herein as a primary zone, that is sufficiently hot to cause the component of the nongaseous precursor to be transferred into the gas phase of a flowing stream in the flame reactor, followed by a particle nucleation from the gas phase. In some embodiments, the temperature in at least some portion of this primary zone, and sometimes only in the hottest part of the flame, is high enough so that substantially all of materials flowing through that portion of the primary zone are in the gas phase. The component of the nongaseous precursor may enter the gas phase by any mechanism. For example, the nongaseous precursor may simply vaporize, or the nongaseous precursor may decompose and the component enter the gas phase as part of a decomposition product. Eventually, however, the component then leaves the gas phase as particle nucleation and growth occurs. Removal of the component from the gas phase may involve simple condensation as the temperature cools or may include additional reactions involving the component that results in a non-vapor reaction product. In addition to this primary zone where the component of the nongaseous precursor is transferred into the gas phase, the flame reactor may also include one or more subsequent zones for growth or modification of the nanoparticulates. In most instances, the primary zone will be the hottest portion within the flame reactor.

By "component" it is meant at least some identifiable portion of the nongaseous precursor that becomes a part of the particle, e.g., comprising the host material, emissive material and emission modifier. For example, the component could be the entire composition of the nongaseous precursor when that entire composition is included in the particle comprising the host material, emissive material and emission modifier. More often, however, the component will be something less than the entire composition of the nongaseous precursor, and may be only a constituent element present in both the composition of the nongaseous precursor and the particle comprising the host material, emissive material and emission modifier. For example, it is often the case that in the flame reactor the nongaseous precursor decomposes, and one or more than one element in a decomposition product then becomes part of the particle comprising the host material, emissive material and emission modifier, either with or without further reaction of the decomposition product.

In some cases, it is desirable to produce the particles comprised in the composition as nanoparticles that are maintained in a dispersed state by a matrix, since in this way the tendency for the nanoparticles to agglomerate is obviated or alleviated. This is conveniently achieved by a gas dispersion process in which a flowing gas dispersion is generated such that dispersion includes a disperse phase dispersed in and suspended by a gas phase. As generated, the gas dispersion has a disperse phase of droplets of a precursor medium comprising a liquid vehicle and at least two precursors, at least one of the precursors being a precursor to the emissive material and emission modifier and at least one of the precursors being a precursor to the host material. After generating the gas dispersion, the gas dispersion is processed in a particle forming step, in which liquid is removed from the droplets of the precursor medium and particles are formed that include nanoparticulates dispersed in the matrix.

Although the powders produced by the foregoing methods have good crystallinity, it may be desirable to increase the crystallinity (average crystallite size) after production. Thus, the powders can be annealed (heated) for an amount of time and in a preselected environment to increase the crystallinity of the particles. Increased crystallinity can advantageously yield an increased brightness and efficiency of the particles. If such annealing steps are performed, the annealing temperature and time should be selected to minimize the amount of interparticle sintering that is often associated with annealing. According to one embodiment, the powder is preferably annealed at a temperature of from about 600° C. to about 1600° C., more preferably from about 1100° C. to about 1400° C. The annealing can be effected by a variety of methods, including heating in a crucible, in a fluidized bed reactor, agitating while heating, and the like. The annealing time is from one minute to one week; preferably not more than about 4 hours. The oxygen-containing powders are, in some embodiments, annealed in an inert gas, such as argon; a reactive gas, such as forming gas; or in an oxygen-containing gas, such air.

Flowable Media

The compositions described herein can advantageously be used to form flowable media, such as inks, pastes and slurries, for applying a coating comprising the inventive composition onto a substrate. In addition to the composition, such flowable media may comprise one or more of the following: a liquid vehicle, an anti-agglomeration agent, one or more additives (e.g., surfactants, polymers, biocides, thickeners, etc.), other particulates (metallic and/or non-metallic), and other components. The media may be deposited in virtually any printing process to form features, e.g., security features, comprising the compositions of the present invention. A non-limiting list of preferred printing processes includes ink-jet printing, screen printing, intaglio printing, roll printing, lithographic printing and gravure printing.

Uses of the Composition

The compositions described herein can be incorporated into a number of devices, wherein the devices will have significantly improved performance resulting directly from the characteristics of the compositions of the present invention. The devices can include light-emitting lamps and display devices for visually conveying information and graphics. Such display devices include traditional cathode ray tube (CRT)-based display devices, such as televisions, and also include flat panel displays.

The compositions described herein can also be incorporated into a security feature, for example, a security feature on credit cards, driver's licenses, passports, checks, currency, bonds, tickets, tax stamps, banknotes, cigarette pack tear tapes, thin films (e.g., for shrink wrap applications), security thread, ID cards and the like. As used herein, the term "security feature" means a feature, as defined above, that is placed on an article (e.g., a tag or label, a document such as a passport, check, bond, banknote, currency, ticket, etc.), directly or indirectly, for the purpose of authenticating the article.

The compositions can also be incorporated into plastics and/or metal. For example, the compositions can be incorporated into plastics by mixing the compositions with the plastic prior to extrusion. The compositions can also be incorporated onto plastics and/or metal by, e.g., printing inks comprising the compositions on articles made of plastic and/or metal.

The compositions of the invention also may be incorporated into laser applications, for example, as a lasing material to form a tunable or switchable laser.

In other aspects, the compositions of the invention may be employed as switches, e.g., in which a first response to excitation radiation may be controllably switched to a second response to the same excitation radiation by non-destructive and non-invasive means. This may be useful, for example, in optical computing, communication (switches and amplifiers), imaging, sensing and detection.

EXAMPLES

Powder compositions according to some aspects of the invention were prepared comprising yttria as the host material, ytterbium as the emissive material and cerium as the emission modifier. The compositions were prepared using a standard set of conditions in a spray pyrolysis process. An aqueous precursor solution was formed comprising an aqueous solution of metal nitrate salts. The total precursor concentration was 8.0 weight percent calculated as the ratio of the mass of the oxide product produced to the total mass of the precursor solution. The liquid solution was atomized using ultrasonic transducers at a frequency of 1.6 MHz. Air was used as a carrier gas and the aerosol was carried through a tubular furnace having a temperature of 900° C. The total residence time in the furnace was less than about 4 seconds. The molar ratio of yttrium to ytterbium was 0.85:0.15.

Example 1

$Y_2O_3$:Yb, Ce was manufactured from a precursor solution comprising yttrium nitrate, ytterbium nitrate and cerium nitrate. The precursor composition was prepared using a concentration of 5 wt %. The molar ratio of yttrium, ytterbium and cerium was 0.85:0.15:0.0011. The solution was atomized and pyrolyzed to prepare a powder. The powder produced was heat treated at a temperature of 1300° C. for 1 hour to produce a phosphor with a small particle size.

Example 2

$Y_2O_3$:Yb, Ce was manufactured from a precursor solution comprising yttrium nitrate, ytterbium nitrate and cerium nitrate. A precursor comprising of yttrium nitrate, ytterbium nitrate and cerium nitrate was prepared using a concentration of 5 wt %. The molar ratio of yttrium, ytterbium and cerium was 0.85:0.15:0.000016. The solution was atomized and pyrolyzed to prepare a powder. The powder was heat treated at a temperature of 1350° C. for 3 hours to produce a powder with an average particle size of 3 microns.

Example 3

$Y_2O_3$:Yb, Ce was manufactured from a precursor solution comprising yttrium nitrate, ytterbium nitrate and cerium nitrate. A precursor comprising of yttrium nitrate, ytterbium nitrate and cerium nitrate was prepared using a concentration of 5 wt %. The molar ratio of yttrium, ytterbium and cerium was 0.85:0.15:0.00013. The solution was atomized and pyrolyzed to prepare a powder. The powder was heat treated at a temperature of 1350° C. for 3 hours to produce a powder with an average particle size of 3 microns.

Example 4

$Y_2O_3$:Yb, Ce was manufactured from a precursor solution comprising yttrium nitrate, ytterbium nitrate and cerium nitrate. A precursor comprising of yttrium nitrate, ytterbium nitrate and cerium nitrate was prepared using a concentration of 5 wt %. The molar ratio of yttrium, ytterbium and cerium was 0.85:0.15:0.0004. The solution was atomized and pyrolyzed to prepare a powder. The powder was heat treated at a temperature of 1350° C. for 3 hours to produce a powder with an average particle size of 3 microns.

Example 5

$Y_2O_3$:Yb, Ce was manufactured from a precursor solution comprising yttrium nitrate, ytterbium nitrate and cerium nitrate. A precursor comprising of yttrium nitrate, ytterbium nitrate and cerium nitrate was prepared using a concentration of 5 wt %. The molar ratio of yttrium, ytterbium and cerium was 0.85:0.15:0.0012. The solution was atomized and pyrolyzed to prepare a powder. The powder was heat treated at a temperature of 1350° C. for 3 hours to produce a powder with an average particle size of 3 microns.

Example 6

$Y_2O_3$:Yb, Ce was manufactured from a precursor solution comprising yttrium nitrate, ytterbium nitrate and cerium nitrate. A precursor comprising of yttrium nitrate, ytterbium nitrate and cerium nitrate was prepared using a concentration of 5 wt %. The molar ratio of yttrium, ytterbium and cerium was 0.85:0.15:0.002. The solution was atomized and pyrolyzed to prepare a powder. The powder was heat treated at a temperature of 1350° C. for 3 hours to produce a powder with an average particle size of 3 microns

Example 7

Measurement of Sample from Example 6

Luminescent measurements were made using a Photon Technology International's (PTI) custom designed spectrometer equipped with a Xenoflash lamp and Hamamatsu NIR cooled PMT module detector. Standard run conditions using PTI's Felix software were 940 nm excitation, 1030 nm emission, 250 channels, 30 microseconds integration time, 2 averages, 20 shots, and 50 shots per second. A sample of the material from Example 6 was loaded in a solid sample holder and no excitation or emission filters were used.

Figure 3:
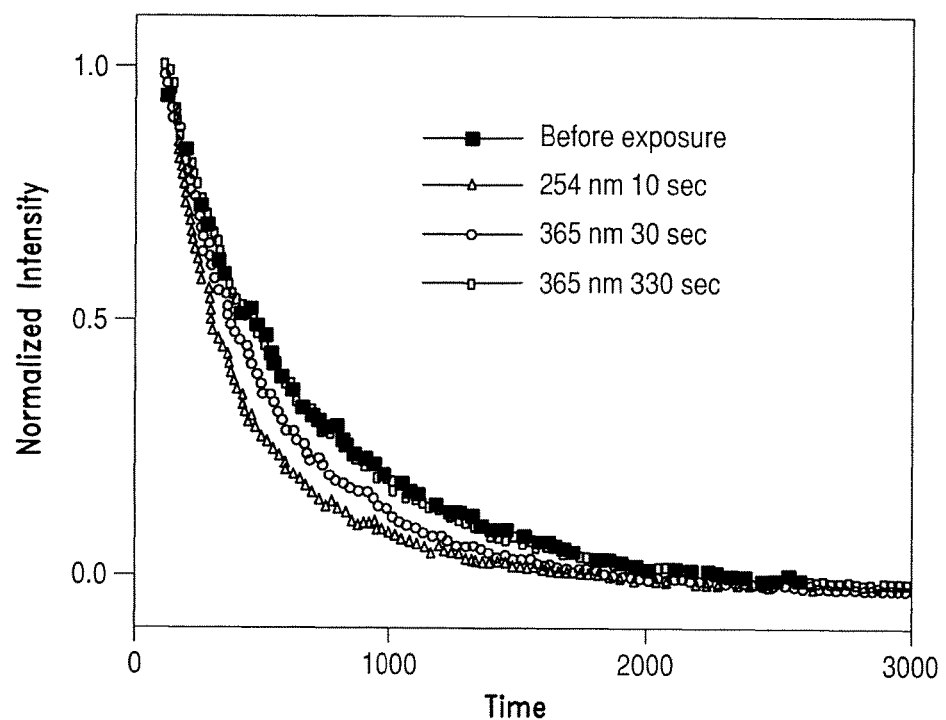
FIG. 3 is a graph illustrating different responses to a first electromagnetic radiation of a composition manufactured according to Example 6, according to one embodiment of the present invention.

After the powder from Example 6 was loaded into the powder sample holder, and an initial spectrum was taken, the powder was exposed to 254 nm radiation for 10 seconds followed by exposure to 365 nm radiation for 30 seconds, and then for 300 seconds using a 0.16 amp Entela model UVGL-25 multi-band Mineralight 254/365. A spectrum was taken after each exposure. FIG. 3 presents a composite graph of the normalized intensity as a function of time for the sample from Example 6: (a) before exposure, (b) after exposure to 254 nm radiation for 10 seconds; (c) after exposure to regeneration radiation at 365 nm for 30 seconds; and (d) after exposure to regeneration radiation at 365 for an additional 300 seconds. This example shows that the composition of Example 6 provides different responses before and after exposure to 254 nm radiation, and may be successfully regenerated after exposure to 365 nm radiation.

Example 8

Measurement of Sample from Example 3

Luminescent measurements were made using a Photon Technology International's (PTI) custom designed spectrometer equipped with a Xenoflash lamp and Hamamatsu NIR cooled PMT module detector. Standard run conditions using PTI's Felix software were 940 nm excitation, 1030 nm emission, 250 channels, 30 microseconds integration time, 2 averages, 20 shots, and 50 shots per second. A sample of the material from Example 3 was loaded in a solid sample holder and no excitation or emission filters were used.

After the powder from Example 3 was loaded into the powder sample holder, and an initial spectrum was taken, the powder was exposed to 254 nm radiation for 5 seconds and 40 seconds. The sample was then exposed to 365 nm radiation for 5, 10, 20, 60 and 120 seconds using a 0.16 amp Entela model UVGL-25 multi-band Mineralight 254/365. A spectrum was taken after each exposure. FIG. 4(a) shows the dependence of decay rate on 254 nm radiation. FIG. 4(b) shows the regenerability upon exposure to regeneration electromagnetic radiation. FIG. 4(c) presents an expansion of the decay curves (time vs. intensity) for the sample from Example 3 after exposure to 245 nm radiation and 365 nm radiation.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions. All U.S. and foreign patent documents discussed above are hereby incorporated by reference into the Detailed Description of the Preferred Embodiment.

What is claimed is:

1. A method for authenticating an article by using a regenerable composition comprising a plurality of forms having a plurality of responses, the method comprising:

subjecting the composition to a first electromagnetic radiation and generating a first response;

applying a second electromagnetic radiation to transform the composition from a first form having the first response to a second form having a second response to the first electromagnetic radiation that is different from the first response; and subjecting the composition to the first electromagnetic radiation and generating the second response, wherein the composition comprises a host material, an emissive material, and an emission modifier, and wherein the composition is incorporated into a security feature for authenticating the article.

2. The method of claim 1, wherein the first response and/or the second response comprise electromagnetic radiation in the ultraviolet spectrum.

3. The method of claim 1, wherein the first response and/or the second response comprise electromagnetic radiation in the infrared spectrum.

4. The method of claim 1, wherein the first response and/or the second response comprise electromagnetic radiation in the visible spectrum.

5. The method of claims claim 1, wherein the composition exhibits a regenerated first response to the first electromagnetic radiation after exposure to a third electromagnetic radiation.

6. The method of claim 1, wherein the host material comprises an oxygen-containing compound selected from the group consisting of $Y_2O_3$, $Y_2GdAl_5O_{12}$, $Y_3Al_5O_{12}$, $Y_3Al_4GaO_{12}$, $YBO_3$, $Y_{0.76}Gd_{0.24}BO_3$, $YPO_4$, $YSiO_5$, $LaBO_3$, $LaPO_4$, $La_2O_3$, $LaAlO_3$, $LuAlO_3$, $La_3Al_5O_{12}$, $LaSiO_5$ and $ReP_5O_{14}$, a sulfide, a fluoride, an oxynitride, an oxysulfide, and an oxyfluoride.

7. The method of claim 1, wherein the emissive material and/or the emission modifier comprise a lanthanide or a transition metal.

8. The method of claim 1, wherein the composition comprises substantially spherical particles.

9. The method of claim 1, wherein the composition has a particle size distribution such that at least about 90 volume percent of the particles are not larger than twice the average particle size.

10. The method of claim 1, further comprising printing the composition onto the article.

* * * * *